United States Patent [19]

Licata

[11] 4,387,921
[45] Jun. 14, 1983

[54] CONTACT LENS APPLICATION

[76] Inventor: Joseph G. Licata, 2495 Queensbury, Pasadena, Calif. 91104

[21] Appl. No.: 264,836

[22] Filed: May 18, 1981

Related U.S. Application Data

[63] Continuation of Ser. No. 101,428, Dec. 10, 1979, abandoned.

[51] Int. Cl.³ .............................................. A61F 9/00
[52] U.S. Cl. ................................................. 294/1 CA
[58] Field of Search .......... 294/1 CA, 1 R, 20, 64 R; 128/303, 249, 233; 206/5.1; 351/160

[56] References Cited

U.S. PATENT DOCUMENTS 3,139,298 6/1964 Grabiel ........................... 294/1 CA
4,097,081 6/1978 England ......................... 294/1 CA Primary Examiner—James B. Marbert
Attorney, Agent, or Firm—David O'Reilly

[57] ABSTRACT

A contact lens applicator comprised of an elongated member having a spherical cup on one end and a spherical cavity in the other. The elongated member is constructed of a relatively stiff material. The spherical cup and cavity on each end of the elongated member are provided with brightly colored targets on which to focus during installation and removal of contact lenses.

11 Claims, 7 Drawing Figures

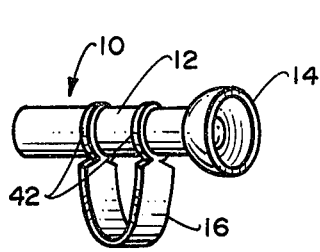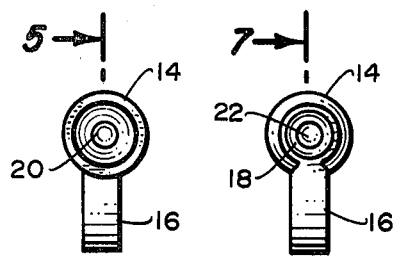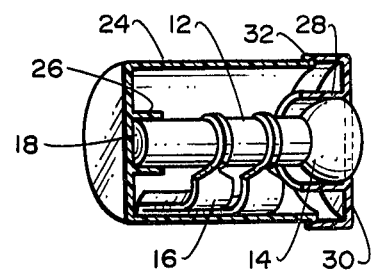
Fig. 1.  Fig. 2.  Fig. 3.  Fig. 4.
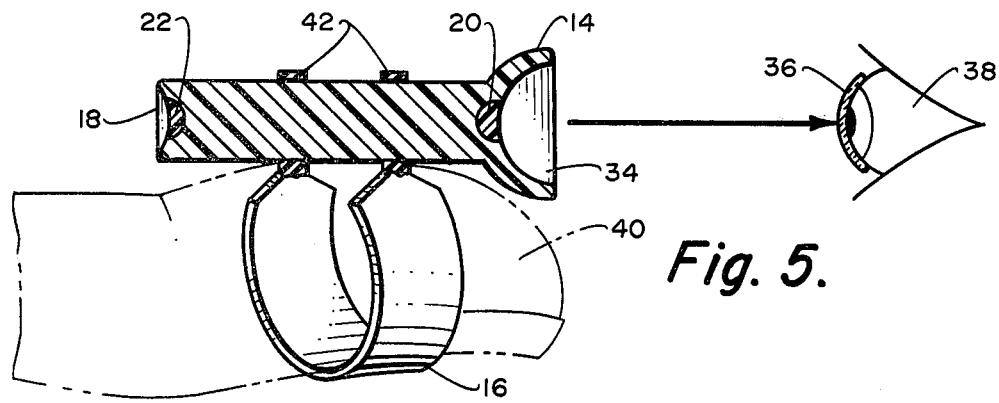
Fig. 5.
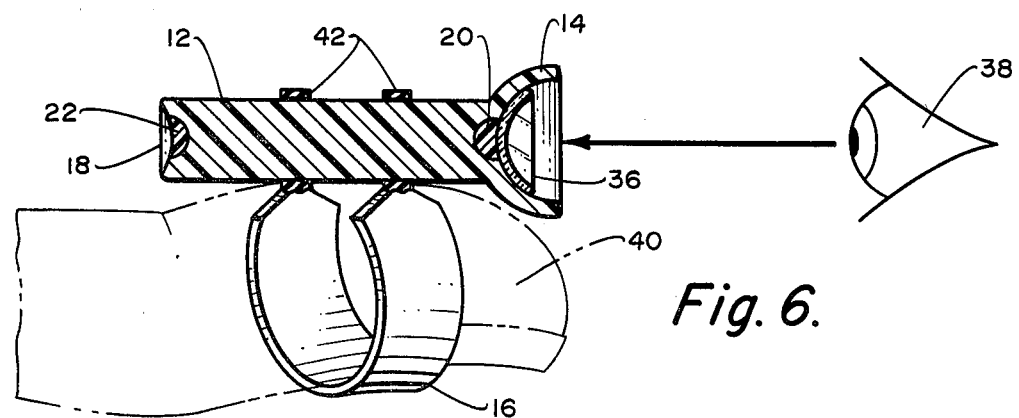
Fig. 6.
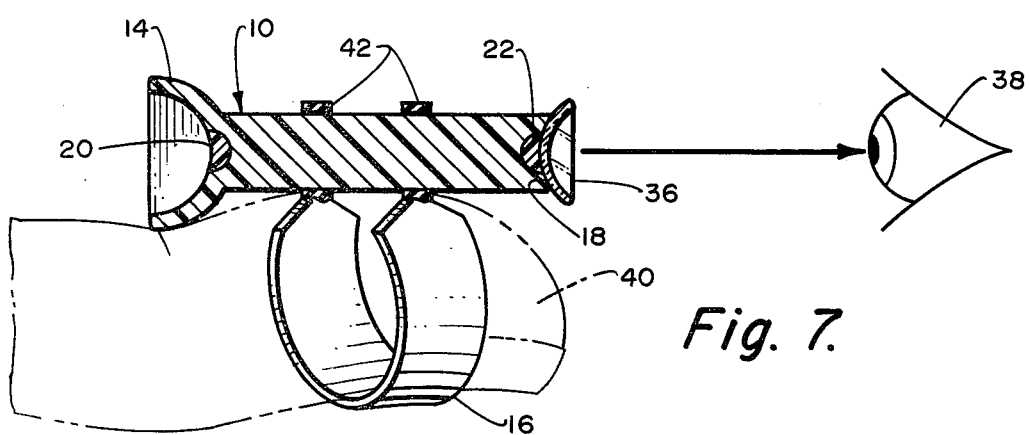
Fig. 7.

CONTACT LENS APPLICATION

This application is a continuation, of application Ser. No. 101,428, filed 12/10/79 now abandoned.

BACKGROUND OF THE INVENTION

This invention relates to a contact lens applicator and more particularly relates to an applicator which assists in correct installation of a contact lens.

Presently contact lens wearers for the most part rely on manual dexterity for installation of contact lenses. That is they place the contact lens on the tip of a finger, usually the index finger, and place the lens over the pupil while spreading the eyelids with the thumb of one hand and the finger of the other. This frequently results in a misplaced lens (i.e. not centered over the pupil properly). While some misplacement can be tolerated because some slight adjustment can be made after the lens is on the eyeball it is unsatisfactory to do so because it means applying some pressure to the eyeball to slide the lens to the correct position. Poking at the eyeball in this manner is unsatisfactory for the obvious reason that damage to the eyeball could result among other things. Further, since the advent of bifocal contact lenses correct placement is even more critical. Even the slightest misplacement can result in a loss of the full use and capability of the bifocal lens as well as causing distorted vision in some instances.

To solve these problems devices for application of contact lenses have been either manufactured or proposed. One such device is an elongated flexible rod having a flexible suction cup on one end. To remove a contact lens the suction cup is pressed against the lens which is lifted off the eyeball by the small suction created. Again, the undesirable application of pressure to the eyeball is necessary. Further this device cannot be used to install the lens.

SUMMARY OF THE INVENTION

The purpose of the present invention is to provide a contact lens applicator suitable for both installation and removal of contact lenses.

The present invention is comprised of an elongated stiff member or rod which has a spherical cup on one end and a spherical cavity on the other. The contact lens applicator of the present invention is preferably constructed of a relatively inflexible non-toxic material such as a nylon or other suitable plastic. To assist in application and removal of contact lenses a brightly colored target is provided at the center of the spherical cup and cavity.

To remove a contact lens the spherical cup is wetted with a suitable contact lens wetting solution. The cup is then placed gently over the lens while focussing on the brightly colored target in the cup. The target allows the spherical cup to make intimate contact with the contact lens allowing it to be gently lifted off the eyeball without the application of any pressure.

To install a contact lens the spherical cavity in the other end of rod is wetted with a wetting solution. This may be accomplished with an eyedropper or by dipping the end of the rod in the solution. The contact lenses is also wetted and is then placed on the wetted spherical cavity. The lens is then brought up to the eye on the end of the rod with the eyelids being spread as before. By focussing with the eye on the target as the lens is brought into contact with the eyeball correct placement is easily and comfortably assured.

It is one object of the present invention to provide a contact lens applicator which permits simple easy placement and removal of contact lenses.

Another object of the present invention is to provide a contact lens applicator which minimizes danger of excessive pressure being applied to the eye.

Another object of the present invention is to provide a contact lens applicator which has means to assure correct placement of a lens in the eye.

Still another object of the present invention is to provide a contact lens applicator having targets for focussing on during placement and removal of contact lenses.

Other objects, advantages and novel features of the invention will become apparent from the following detailed description of the invention when considered in conjunction with the accompanying drawings, wherein:

FIG. 1 is a perspective view of a contact lens applicator according to the invention;

FIG. 2 is a view of the concave cup end of the contact lens applicator;

FIG. 3 is a view of the end of the contact lens applicator opposite the concave cup.

FIG. 4 is a perspective view of the contact lens applicator in its protective container.

FIG. 5 and 6 are sectional views taken at 5—5 of FIG. 2 showing removal of a contact lens; and FIG. 7 is a sectional view taken at 7—7 of FIG. 3 showing placement of a contact lens.

DESCRIPTION

Referring to the drawings there is shown a contact lens applicator generally indicated at 10 comprised of an elongated rod 12 having a concave cup 14 on one end and a finger strap 16 which will be described in greater detail hereinafter. The applicator 10 is constructed of a relatively stiff non-toxic material such as nylon or a suitable plastic. At the opposite end of the elongate rod 12 from the concave cup 14 there is a small concave cavity 18.

A unique feature of the contact lens applicator 10 is the provision of targets 20 and 22 in the concave cup 14 and cavity 18. These targets are in the form of a brightly colored plug, preferably red, which are inserted in holes at the bottom of the respective cavities. These targets provide assistance in the installation and removal of a contact lens and assure accurate, comfortable placement.

Because the applicator 10 must be kept clean and free of damage a container 24 for storing the applicator is provided as shown in FIG. 4. The container has sockets 26 and 28 for receiving the respective ends of the applicator 10. The socket 26 on the closed end of the container 24 loosely fits the end of the applicator as shown. The socket 28 is provided on the cap 30 of the container and snugly fits over the concave cup. The cap and container are provided with suitably nap rings 32 for holding the cap on the container. The snug fit of socket 28 acts to retain the applicator 10 attached to the cap so that when the cap is removed the applicator comes with it. The container 24 may or may not be filled with a suitable wetting solution as desired.

The concave cup 14 is used for removing a contact lens. To accomplish this purpose the cup 14 is made slightly larger than a contact lens as shown at 34. With the hemispherical shape of the cup 14 conforming the curvature of the contact lens 36 this assures that the lens will fit completely inside the cup 14.

To remove a contact lens the concave cup is first wetted with a suitable wetting solution which may be clean water. The cup 14 is then brought into contact with the lens 36 on the eye 38 as shown in FIG. 5 while focussing on the target 20 which will assure coverage of the lens with the cup 14. The application 10 is then withdrawn as shown in FIG. 6 removing the contact lens 36 from the eye 38. The combination of the concave cup is larger than the lens and the surface tension created by the wetting solution gently lifts the contact lens from the eye 38 without any pressure of force being applied to the eyeball.

To install a contact lens the opposite end of the rod 12 is used. On this end a small, shallow cavity 18 is provided to simply hold the lens 36 during insertion. The cavity is first wetted with a wetting solution and the contact lens 36 placed in the cavity. Since the lens 36 is extremely small and light it is easily retained in the cavity 18 by a very small force produced by the small shallow cavity and the surface tension of the wetting solution. The contact lens 36 is then brought into contact with the eye 38 while focussing on the target. The instant the lens 36 contacts the eye the applicator 10 may be withdrawn leaving the lens 36 accurately and confortably placed in the eye.

The applicator 10 may be held between the thumb and forefinger during use if desired. However, since the applicator 10 is necessarily rather small a flexible finger strip 16 is provided to allow manipulation with a single finger 40 if desired. This will leave the thumb of the hand being used to manipulate the applicator free for use in spreading the lower eyelid. The strap 16 is constructed of a soft flexible elastic material and has loops 42 which slide over the rod 12 to hold the strap on the applicator. Thus the strap may be easily removed if not used.

As was stated previously the targets 20 and 22 are in the form of plugs but may be provided in other forms. For example they could be formed by coloring the material itself or by an adhesive dot which fits the bottom of the cavity. The plug is preferred because it will not wear out and can easily and inexpensively be fabricated.

Obviously, many modifications and variations of the present invention are possible in light of the above teachings. It is therefore to be understood that the full scope of the invention is not limited to the details described herein and may be practiced otherwise than as specifically described.

What is claimed is:

1. A contact lens applicator comprising:
   an elongated shaft;
   a first concave cup on one end of said elongated shaft; said first concave cup being substantially larger than the average contact lens;
   a second concave cup on the other end of said elongated shaft; said second concave cup being substantially smaller than the average contact lens;
   target means centrally located in each of said first and second concave cups;
   said elongated shaft and said first and second concave cups being constructed of a stiff material;
   whereby said first concave cup can be used with a wetting solution to remove a contact lens from the eye, said second concave cup can be used with a wetting solution to place a contact lens in the eye, said target means serving as a focal point during the removal or placement of a contact lens so that removal or placement can be accomplished without the use of a mirror.

2. The contact lens applicator according to claim 1 in which the first and second concave cups are of an integrally formed homogeneous construction with the elongated shaft.

3. The contact lens applicator according to claim 1 including strap means on said shaft for strapping said applicator on a finger during use.

4. The contact lens applicator according to claim 1 wherein said shaft is comprised of an acetal resin plastic.

5. The contact lens applicator according to claim 1 wherein said target means comprises a brightly colored plug inserted in the center of each concave cup.

6. The contact lens applicator according to claim 1 wherein said shaft is cylindrical.

7. The contact lens applicator according to claim 1 wherein said shaft and concave cups are comprised of an acetal resin plastic.

8. A method of removing a contact lens from the eye comprising:
   forming a concave cup of stiff material substantially larger than said contact lens;
   applying wetting solution to the interior surface;
   mating the interior surface of the concave cup with the surface of the contact lens in the eye with minimum pressure applied so that the concave cup substantially surrounds the contact lens;
   withdrawing said concave cup whereby said contact lens is gently lifted from the surface of the eye.

9. The method according to claim 8, including forming a target in the interior surface of said concave cup whereby said contact lens may be removed without the aid of a mirror.

10. The method according to claim 8 in which the step of forming said concave cup includes forming an integral homogenous shaft of the same stiff material whereby said concave cup may be easily manipulated with the fingers.

11. The method according to claim 10 including forming a second integral homogenous concave cup smaller than the average contact lens on the opposite end of said elongate shaft from said concave cup larger than the contact lens.

* * * * *